(12) United States Patent
Kopperschmidt

(10) Patent No.: US 12,138,375 B2
(45) Date of Patent: Nov. 12, 2024

(54) METHOD AND APPARATUS FOR MONITORING THE MEMBRANE COUPLING IN A PRESSURE MEASUREMENT SYSTEM

(71) Applicant: Fresenius Medical Care Deutschland GmbH, Bad Homburg (DE)

(72) Inventor: Pascal Kopperschmidt, Dittelbrunn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 496 days.

(21) Appl. No.: 17/442,680

(22) PCT Filed: Mar. 20, 2020

(86) PCT No.: PCT/EP2020/057727
§ 371 (c)(1),
(2) Date: Sep. 24, 2021

(87) PCT Pub. No.: WO2020/193388
PCT Pub. Date: Oct. 1, 2020

(65) Prior Publication Data
US 2022/0184291 A1    Jun. 16, 2022

(30) Foreign Application Priority Data
Mar. 25, 2019 (DE) .................... 10 2019 107 604.8

(51) Int. Cl.
*A61M 1/36* (2006.01)
(52) U.S. Cl.
CPC ....... *A61M 1/3641* (2014.02); *A61M 2205/18* (2013.01); *A61M 2205/3331* (2013.01)
(58) Field of Classification Search
CPC ............ A61M 1/3641; A61M 2205/18; A61M 2205/3331; G01L 9/0026; G01L 9/0089; G01L 19/0023; G01L 27/007
See application file for complete search history.

(56) References Cited

FOREIGN PATENT DOCUMENTS

| DE | 198 02 615 | 8/1999 |
|---|---|---|
| DE | 101 15 991 | 4/2002 |
| WO | WO 03/093780 | 11/2003 |
| WO | WO 2015/099932 | 7/2015 |

*Primary Examiner* — Thuan D Dang
(74) *Attorney, Agent, or Firm* — Jacobson Holman PLLC

(57) ABSTRACT

The present invention relates to a method and to an apparatus for continuously monitoring the membrane coupling in a pressure measurement system in a extracorporeal circuit of a blood treatment machine. The invention enables the continuous monitoring of the functionality of the pressure measurement system without an interruption of any blood treatment being necessary.

14 Claims, 3 Drawing Sheets

METHOD AND APPARATUS FOR MONITORING THE MEMBRANE COUPLING IN A PRESSURE MEASUREMENT SYSTEM

The present invention relates to a method and to an apparatus for monitoring, preferably continuously, the membrane coupling/membrane connection in a pressure measurement system in the extracorporeal circuit of a blood treatment machine.

Pressure measurements in an extracorporeal circuit of a blood treatment machine conventionally take place either via depressurization tubes containing air at the extracorporeal tube segments, under certain circumstances with integrated balance vessels or compliance vessels or free of air directly via a membrane that is integrated in the tube segment and that is connected to a pressure plunger (pressure dome). A deformation of the membrane by means of the pressure dome that is proportional to a certain pressure can be measured by the coupling of the membrane to the pressure dome and the corresponding pressure acting on the membrane can be determined.

The determined measurement values of the pressure, in particular of the supply pipe pressure in the extracorporeal circuit that is negative with respect to the atmosphere, can be used for monitoring rheological blocks, for correcting flow rates of peristaltic pumps, for a leak tightness test of the tube system, for monitoring pressure-generating connected actuators and, optionally, for detecting vital parameters of the patient.

Different methods of pressure measurement are known from the prior art. In this respect, a pressure measurement that takes place via a deaerated membrane has certain advantages over a pressure measurement via a pressure line that is filled with air.

For example, due to the reduced mechanical compliance of the air-free membrane, pressure changes can be directly detected by means of a pressure measurement process that uses an air-free membrane. In contrast to this, depressurization lines containing air increase the extracorporeal blood volume, cause air-to-blood contact surfaces that are linked with an increased risk of thrombosing, and require protectors to avoid a penetration of fluid into the pressure measurement cell. These protectors can clog and interrupt the depressurization.

The pressure measurement using a pressure dome such as is conventionally designed is, however, also problematic. For example, on the measurement of a pressure in the tube having an integrated pressure dome below atmospheric pressure, the coupling between the membrane and the plunger that detects the membrane position can be partially or completely interrupted. This problem in particular occurs when the membrane in the pressure dome arches inwardly (i.e. away from the pressure dome in the direction of the lumen of a tube in which the membrane is installed) due to the negative pressure and the measurement plunger can only follow the membrane conditionally, i.e. not completely.

In this case, an unwanted decoupling of the membrane from the pressure plunger or the pressure dome occurs and the measurement accuracy of the pressure measurement system falls since a partial or complete release of the coupling produces an erroneous measurement of the pressure in the tube segment. Systems that need or require pressure in the tube for their monitoring or parameterization work incorrectly under these conditions and can thus endanger the therapy or the patient.

To avoid this problem, the coupling of the membrane to the pressure dome is conventionally monitored to thus monitor the functionality of the pressure measurement system. The monitoring of the coupling between the membrane and the plunger typically takes place in this process by a pressure test in which the pressure present in the tube system is reduced in a controlled manner and the value determined by the pressure measurement system is simultaneously checked for plausibility.

This conventional process has the significant disadvantage, however, that an extracorporeal blood treatment optionally carried out by the blood treatment machine in whose extracorporeal circuit the pressure measurement takes place has to be interrupted during the carrying out of the method for monitoring the membrane coupling.

In other words, the conventional monitoring method cannot be carried out continuously or with an ongoing blood treatment. The conventional method consequently only provides a snapshot of the connection between the membrane and the pressure dome of the pressure measurement system at the time of the measurement. A changing coupling between the membrane and the pressure dome during the blood treatment cannot be detected by this conventional monitoring method.

It is, however, essential for ensuring the safety of the patient to ensure an unrestricted functionality of the blood treatment machine used during an ongoing blood treatment. It is thus the underlying object of the invention to provide a method for a continuous monitoring of the membrane coupling in a pressure measurement system in an extracorporeal circuit of a blood treatment machine.

This object is achieved by a method of the invention for monitoring, preferably continuously monitoring, the membrane coupling in a pressure measurement system in an extracorporeal circuit of a blood treatment machine comprising the steps: —detecting periodic pressure pulses occurring in the extracorporeal circuit; —a frequency analysis based on the detected periodic pressure pulses for calculating at least one Fourier coefficient; —comparing the at least one calculated Fourier coefficient with respect to its intensity with at least one associated reference value; and—outputting a signal when the comparison shows that, with respect to its intensity, the at least one Fourier coefficient differs from the associated reference value beyond a predetermined tolerance threshold value, and by an apparatus of the invention for carrying out the method of the invention having a pressure measurement system that has a pressure dome and a membrane coupled to the pressure dome and having a control unit that is configured to carry out the method. A further aspect of the invention relates to a blood treatment machine containing the apparatus of the invention. Further advantages further developments of the invention form the subject of the dependent claims.

In accordance with the invention, a method for a monitoring, preferably a continuous monitoring, of the membrane coupling in a pressure measurement system in an extracorporeal circuit of a blood treatment machine comprises the following steps: detecting periodic pressure pulses occurring in the extracorporeal circuit; a frequency analysis based on the detected periodic pressure pulses for calculating at least one Fourier coefficient; comparing the at least one calculated Fourier coefficient with respect to its intensity with at least one associated reference value; and outputting a signal when the comparison shows that, with respect to its intensity, the at least one Fourier coefficient differs from the associated reference value beyond a predetermined tolerance threshold value.

The central idea of the present invention in other words comprises also continuously monitoring the functionality of the pressure measurement system during the operation of the pressure measurement system, e.g. during a blood treatment, by a continuous analysis of the measurement behavior of the pressure measurement system.

The signal can be of any desired kind; it can be an internal signal, i.e. a signal not perceptible to the outside, or an external signal, i.e. a signal that is perceivable for a user such as an optical and/or acoustic alarm signal. Said internal signal can, for example, be data that trigger a specific measure such as an error routine.

A malfunction of the pressure measurement system, in particular in the form of a defective or only insufficient coupling between the membrane and the pressure dome/pressure plunger of the pressure measurement system, is in particular reflected in a reduced intensity of the Fourier coefficients of a Fourier series with an increasing frequency underlying the periodically measured pressure pulses. In other words, it is characteristic for a pressure measurement system having an insufficient membrane coupling that low frequency pressure pulses being harmonically of a lower order can still be appropriately detected, but with higher frequency pressure pulses being harmonically of a higher order, the signal transmission damped or degraded by the decoupling between the membrane and the pressure dome/pressure plunger results in a degraded signal detection and thus in Fourier coefficients of reduced intensity. This principle is shown figuratively in FIG. 1.

Figure 2:
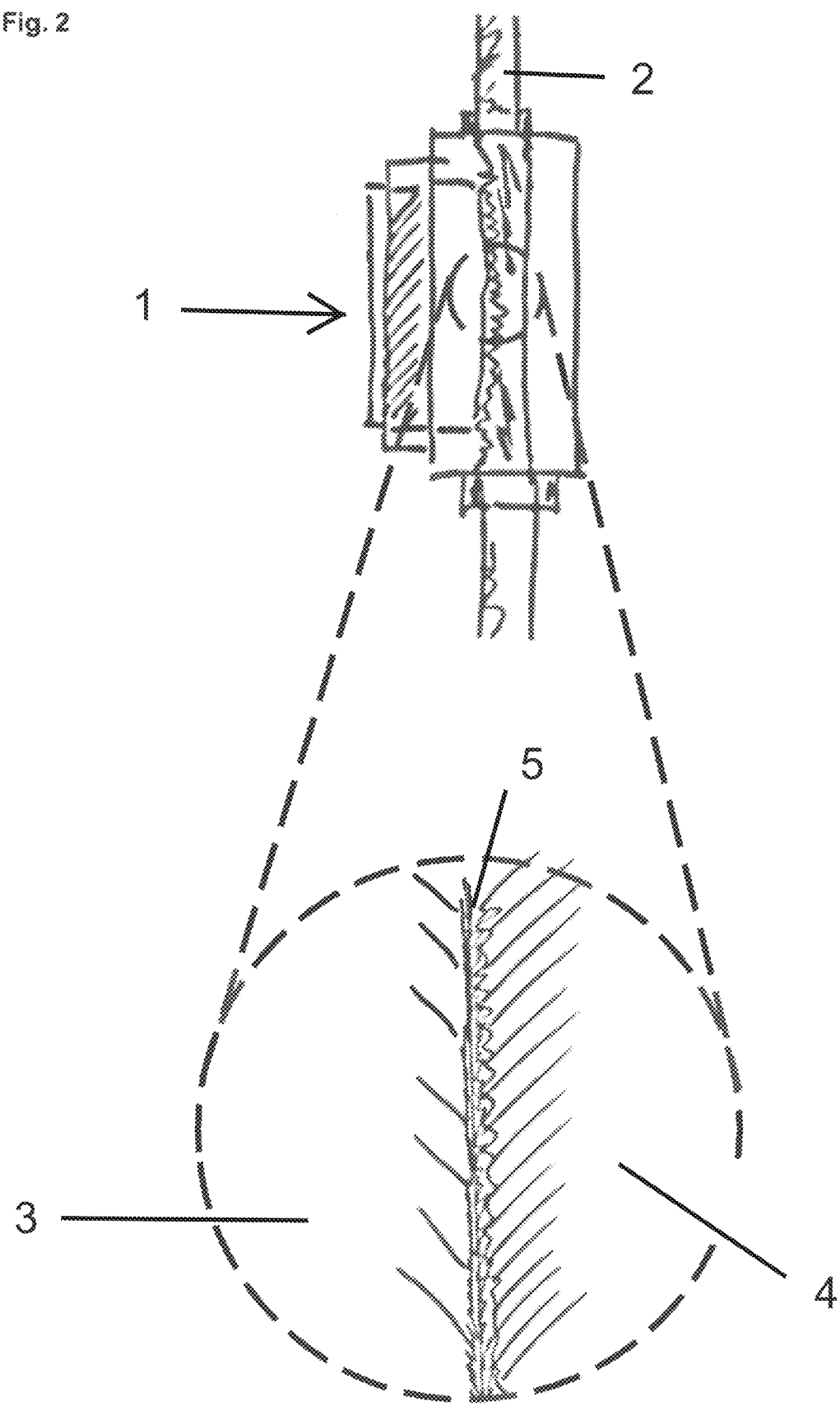
FIG. 2 illustrates a detailed view of the state of a pressure measurement system with a good coupling of the membrane to the measurement plunger of the pressure measurement system.
Figure 3:
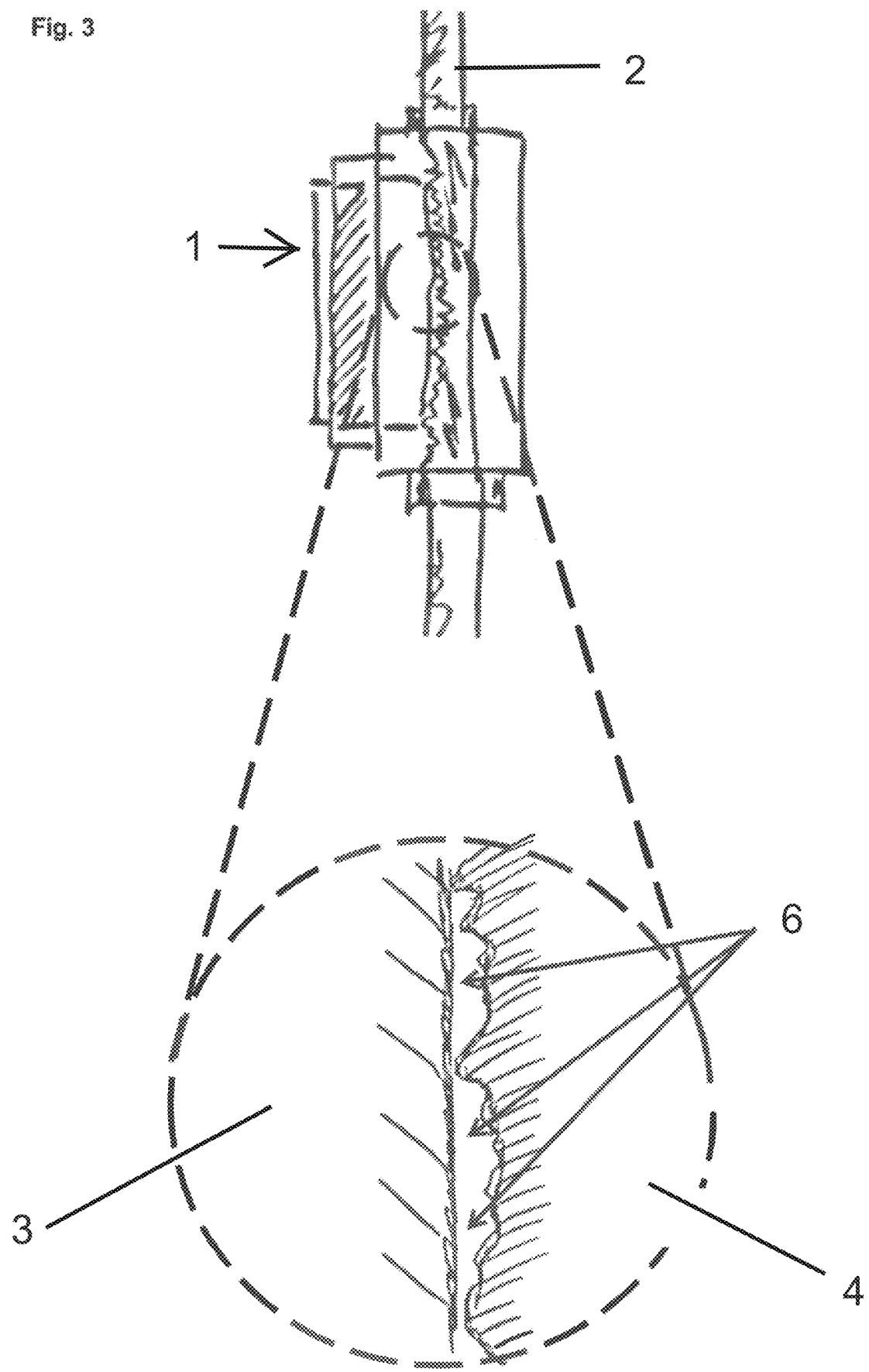
FIG. 3 illustrates a detailed view of the state of a pressure measurement system with a deficient coupling of the membrane to the measurement plunger of the pressure measurement system.

In addition, FIGS. 2 and 3 illustrate the state of a pressure measurement system with a good coupling of the membrane to the measurement plunger of the pressure measurement system (FIG. 2) and with a deficient coupling of the membrane to the measurement plunger of the pressure measurement system (FIG. 3).

As shown in FIG. 2, a pressure measurement system 1 is arranged at a tube line 2 that can be part of an extracorporeal circuit of a blood treatment machine. The pressure measurement system preferably forms a part of the extracorporeal circuit. The pressure measurement system 1 has a pressure dome/measurement plunger 3 and a membrane 4.

As shown in the detailed view in FIG. 2, the membrane 4 contacts the measurement plunger 3 with an optimum or also only sufficient coupling of the membrane 4 to the measurement plunger 3 and thus forms a preferably continuous contact surface 5 between the membrane 4 and the measurement plunger 3.

With such a coupling of the membrane 4 to the measurement plunger 3, pressure-induced deformations of the membrane 4 are directly transmitted to the measurement plunger 3 so that the specificity and measurement accuracy of the pressure measurement system is good or satisfactory.

As shown in FIG. 3, on a deficient coupling of the membrane 4 to the measurement plunger 3 of the pressure measurement system 1, the membrane 4 is not in contact with the measurement plunger 3.

A continuous contact surface 5 is thus not formed between the membrane 4 and the measurement plunger 3; there are rather cavities 6 and/or gas bubbles between the membrane 4 and the measurement plunger 3. The measurement accuracy of the pressure measurement system is reduced in such a state due to the damped or attenuated signal transmission from the membrane 4 to the measurement plunger 3. This effect is in particular reflected in higher frequency signals.

It has proved to be advantageous if the absolute or relative change of the at least one calculated Fourier coefficient is determined with respect to its intensity with regard to the at least one associated reference value on the comparison in a method in accordance with the invention. The at least one reference value or also a plurality of reference values is/are preferably stored or saved beforehand.

Alternatively or additionally, on the comparison, a change of the time progression or trend of the at least one calculated Fourier coefficient is determined with respect to its intensity with regard to a predetermined time change. In other words, the reference value does not necessarily have to be an absolute value, but can also be a specific change rate or another comparison value.

A signal is preferably output when the comparison shows that the intensity of the at least one Fourier coefficient reduces as the frequency of the periodic pressure pulses occurring in the extracorporeal circuit increases.

It has furthermore proved to be advantageous if a plurality of Fourier coefficients of preferably a plurality of higher harmonic Fourier series are calculated that are each compared with an associated reference value. The use of coefficients of a plurality of higher harmonic Fourier series enables a redundant process with increased specificity.

Provision can furthermore additionally be made that a repair attempt, preferably a fully automatic repair attempt is preferably independently or autonomously carried out to improve the membrane coupling or to restore an appropriate membrane coupling in the pressure measurement system when the comparison shows that the at least one Fourier coefficient deviates from the associated reference value beyond a predetermined tolerance threshold value with respect to its intensity.

In other words, the method in accordance with the invention is not necessarily restricted to the output of a signal on the detection of a malfunction of the pressure measurement system, but rather optionally initiates an attempt to remedy the malfunction and/or to restore the functionality of the pressure measurement system or to repair the pressure measurement system.

The repair attempt can comprise the following steps: Applying a positive pressure in the extracorporeal circuit such that the membrane of the pressure measurement system arches toward the pressure dome of the pressure measurement system, whereby any gas bubbles are removed from a contact surface between the membrane and the pressure dome or the pressure plunger. The coupling between the membrane and the pressure dome/pressure plunger is improved by the removal of the gas bubbles.

The invention further relates to an apparatus for carrying out a method in accordance with the invention having a pressure measurement system that has a pressure dome and a membrane coupled to the pressure dome and having a control unit that is configured to carry out the method steps of a method in accordance with the invention. In addition, the apparatus can have a memory in which the reference values are stored or saved.

The pressure measurement system is preferably configured and/or arranged to measure the pressure in an extracorporeal circuit of a blood treatment machine. The pressure measurement system is, for example, arranged in an extracorporeal circuit of a blood treatment machine.

The present invention additionally relates to a blood treatment machine having such an apparatus for carrying out a method in accordance with the invention.

The blood treatment machine here preferably has at least one pump, preferably a peristaltic pump, that conveys a fluid volume intermittently at a specific frequency. The blood treatment machine can, however, also have any desired other actuator that effects periodically recurring pressure pulses in the extracorporeal circuit of the blood treatment machine.

The present invention is generally based on the following considerations: The conveying of volume in extracorporeal tube systems or an extracorporeal circuit of a blood treatment machine as a rule takes place via non-invasive peristaltic pumps that move a volume enclosed in the pump tube segment downstream by a peristaltic movement.

This movement is discontinuous due to the pump heads periodically engaging on the tube section. In other words, the conveying volume of a peristaltic pump is intermittently conveyed. Periodic pressure fluctuations that propagate downstream and upstream of the pump accompany this discontinuous conveying. The periodicity of the pressure fluctuation is derived from the rotational speed of the pump and thus from the incidence or frequency of the conveyed surges of conveying volume of the pump.

These pressure fluctuations can be detected by means of the pressure measurement systems (pressure sensors) arranged in or connected to the extracorporeal tube. Suitable algorithms here enable an analysis of the pressure values, e.g. with respect to their Fourier coefficients.

The Fourier coefficients are in particular suitable to describe or analyze the periodicity of the periodically occurring pressure fluctuations on the basis of the measurement values of the pressure measurement systems. The Fourier coefficients represent the contribution to the total signal of an individual harmonic vibration of a specific periodicity. If a coefficient changes, the contribution of this corresponding periodicity in the total signal has changed.

The frequency analysis of the pressure pulses (or of the pressure measurement values determined in response to the periodic pressure fluctuations) and the determination of the respective frequency-specific contributions to the periodic signal deliver information on the variable quality of the connection between the membrane and the pressure dome or pressure plunger.

Due to the customary shape stability of the pressure pulses (a substantially invariable defined pattern of periodic pressure fluctuations and thus of pressure measurement values or pressure pulses exists for every predetermined setting of the peristaltic pump), a change of the frequency-specific contributions to the pressure signal is very probably due to a reduction in the membrane coupling in the pressure dome.

In other words, a change of the measurement values that is in particular detected by the analysis of the Fourier coefficients indicates, in view of the invariable defined pattern of periodic pressure fluctuations due to the operation of the peristaltic pump, a change of the pressure measurement system itself, in particular a change of the coupling between the membrane and the pressure sensor.

Figure 1:
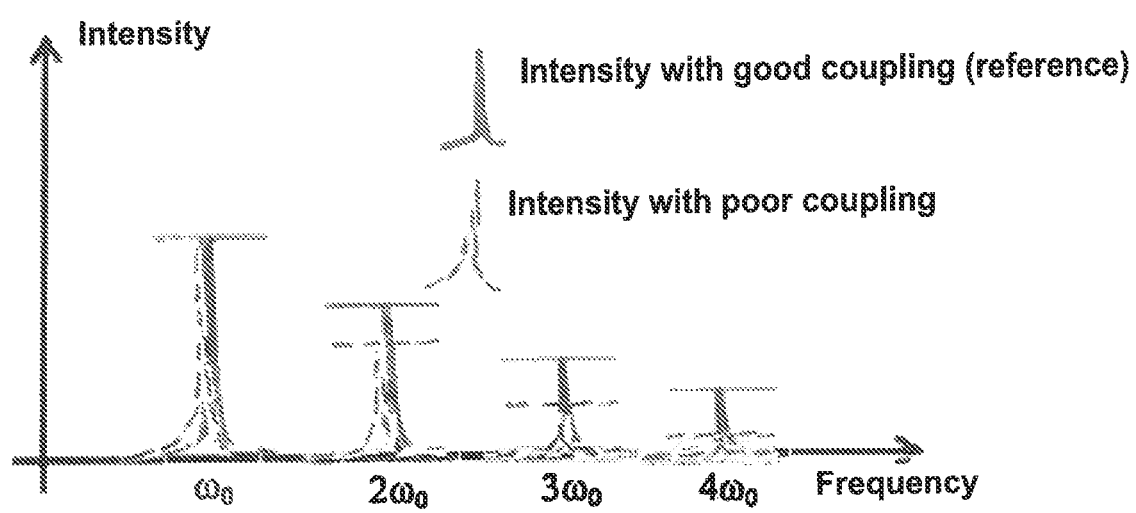
FIG. 1 is a graph, which figuratively depicts the principle of degraded signal detection and thus in Fourier coefficients of reduced intensity in a pressure measurement system.

An attenuation of the higher frequency Fourier coefficients is in particular to be expected on a reduction of the membrane coupling, see FIG. 1. In other words, on a reduction of the coupling of the membrane to the pressure dome, the Fourier coefficients becomes weaker as the frequency level increases.

This is a consequence of a damped or less direct transmission of signals having a high fine frequency structure when the membrane is not, as should actually ideally be the case, directly coupled to the pressure dome.

This effect can be used to continuously monitor the coupling between the membrane and the dome, with an absolute and/or relative change (e.g. relative to specific reference values) of the contributions of the coefficients indicating a change of the coupling.

The invention will be explained further in the following with reference to an embodiment of the invention.

In the present embodiment, a method in accordance with the invention is used to monitor the function of a pressure measurement system, in particular the coupling of a membrane to a pressure dome of the pressure measurement system, in an extracorporeal circuit of a blood treatment machine.

To continuously monitor the coupling between the membrane at the tube segment and a measurement plunger at the pressure dome, the pressure fluctuations starting from the blood pump or other pumps in the extracorporeal circuit are detected by means of the pressure measurement system or of the pressure sensor and are spectrally broken down into components or Fourier coefficients, preferably by means of Fourier analysis, in a suitable processing unit.

These components or Fourier coefficients are compared with reference values with respect to their intensity. If the intensities deviate from the respective reference value by a specific portion or amount, preferably defined beforehand, a detection is made that the transmission of the pressure signal is suboptimal or attenuated and a corresponding signal or a corresponding report is preferably output.

A check or a determination can be made by means of an automatic or manual plausibility check as to what the possible reason for the attenuation of the signal transmission is. The signal transmission can, for example, occur due to a defective coupling of the membrane to the pressure dome.

The comparison of the intensities of the components or Fourier coefficients with corresponding reference values preferably takes place as shown in the following. A corresponding reference value $R_i$ is preferably associated with every calculated intensity $A_i$ so that an absolute or relative change toward the reference ($crit_i$) can be determined (see equation 1).

$$\left| \frac{\partial}{\partial t} A_i \right| > crit_i \qquad \text{Equation 1}$$

Alternatively or additionally, it is also conceivable to monitor the trend or time progression of a specific intensity. In this case, intensity reference values are not absolutely required. It can, for example, be monitored whether the deviation between an intensity $A_i$ and a corresponding reference value $R_i$ goes beyond a specific reference value or a threshold value $crit_i$.

Provision can additionally also be made that the trend progression of the calculated intensity may not exceed or fall below a specific time change to signal an error case (see equation 2).

$$A_i - R_i < crit_i; \quad \frac{A_i - R_i}{R_i} < crit_i \qquad \text{Equation 2}$$

If the change rate of the time progression of an intensity, for example, exceeds a specific predefined change rate or if the change rate of the time progression departs from a predetermined tolerance corridor, a signal is preferably output.

On an identification of a disrupted signal transmission, the pressure measurement system can optionally automatically carry out a repair attempt to eliminate the problem.

In the case of the deficiently connected pressure dome, it can briefly release the membrane on a lightly positive pressure in the tube so that possible air bubbles that contribute to the reduction of the coupling are pushed out of the contact surface between the membrane and the pressure dome due to the membrane arched toward the pressure dome.

The monitoring method in accordance with the invention provides at least the following advantages:

The method can be continuously operated. Any blood treatment thus does not have to be interrupted.

The method of the use of coefficients of a plurality of higher harmonic Fourier series enables a redundant process with increased specificity.

The release of the membrane coupling can be gradually detected and can be compared with a stored reference value.

As a result of the determined deviation between a current measurement value or a Fourier coefficient calculated out of it and a reference value, further tests or methods can preferably be automatically initiated to improve the membrane coupling.

Alternatively or additionally, a signal can also be output in the form of an alarm signal that draws the attention of a user to a probable malfunction of the pressure measurement system and prompts him to remedy the underlying problem.

The individual intensities of the higher harmonic Fourier series or groups of intensities can be compared with one another or respectively with reference values due to the plurality of higher harmonic Fourier series that are typically present in extracorporeal systems having pressure pulse generating actuators such as peristaltic pumps due to the reduced mechanical compliance. This expands the application options of the method in accordance with the invention and increases the significance and sensitivity of the analysis.

The method can be applied using any desired actuators, for example pumps, whose activity results in the generation and propagation of periodic pressure pulses. Even non-peristaltically operating pumps can be used if their conveying rate is modulated by a specific frequency.

It is conceivable that an examination as to whether a membrane coupling problem or another error is present is made within the framework of an error routine that is triggered on the basis of the method of the invention, i.e., if the comparison shows that the at least one Fourier coefficient differs from the associated reference value beyond a predetermined tolerance threshold value with respect to its intensity.

In addition to the continuous monitoring of the coupling of the membrane to the pressure dome, kink points between the actuator (e.g. a pump) generating the pressure pulses and the measurement point of the pressure measurement system in the tube can furthermore be identified.

These kink points that e.g. occur due to a torsion of a tube segment between the sensor and the actuator produce a damping of the signal transmission that can be mathematically represented as a reduction in the intensity values of Fourier coefficients at higher frequencies.

The continuous check of a sufficient connection of a membrane to a pressure dome can furthermore generally be extended to other systems to be mechanically coupled.

They e.g. include membranes for a sound transmission or films for enclosing cavities or hollow spaces. An application of the present method in accordance with the invention to such systems is also covered by the present invention.

The invention claimed is:

1. A method for monitoring the membrane coupling in a pressure measurement system in an extracorporeal circuit of a blood treatment machine comprising the steps:
   detecting periodic pressure pulses occurring in the extracorporeal circuit;
   a frequency analysis based on the detected periodic pressure pulses for calculating at least one Fourier coefficient;
   comparing the at least one calculated Fourier coefficient with respect to its intensity with at least one associated reference value; and
   outputting a signal when the comparison shows that, with respect to its intensity, the at least one Fourier coefficient differs from the associated reference value beyond a predetermined tolerance threshold value.

2. A method in accordance with claim 1, characterized in that, on the comparison, the absolute or relative change or deviation of the at least one calculated Fourier coefficient is determined with respect to its intensity with regard to the at least one associated reference value; and/or in that the signal is a perceptible signal such as an acoustic and/or optical alarm signal or an imperceptible signal such as a signal to trigger an error routine.

3. A method in accordance with claim 1, characterized in that, on the comparison, a change of the time progression or trend of the at least one calculated Fourier coefficient is determined with respect to its intensity with regard to a predetermined time change.

4. A method in accordance with claim 1, characterized in that the signal is output when the comparison shows that the intensity of the at least one Fourier coefficient reduces as the frequency of the periodic pressure pulses occurring in the extracorporeal circuit increases.

5. A method in accordance with claim 1, characterized in that a plurality of Fourier coefficients are calculated that are each compared with an associated reference value.

6. A method in accordance with claim 1 further comprising the step:
   independently carrying out a repair attempt, a fully automatic repair attempt, as an element of an error routine to improve the membrane coupling or to restore an appropriate membrane coupling in the pressure measurement system when the comparison shows that the at least one Fourier coefficient differs from the associated reference value with respect to its intensity beyond a predetermined tolerance threshold value.

7. A method in accordance with claim 6, characterized in that the repair attempt comprises the following steps:
   applying a positive pressure in the extracorporeal circuit such that the membrane of the pressure measurement system arches toward the pressure dome of the pressure measurement system, whereby any gas bubbles are removed from a contact surface between the membrane and the pressure dome or the pressure plunger.

8. An apparatus for carrying out a method in accordance with claim 1, having a pressure measurement system that has a pressure dome and a membrane coupled to the pressure dome and having a control unit that is configured to carry out the method.

9. An apparatus in accordance with claim 8, characterized in that the pressure measurement system is configured and/or arranged to measure the pressure in an extracorporeal circuit of a blood treatment machine.

10. A blood treatment machine having an apparatus in accordance with claim 8.

11. A blood treatment machine in accordance with claim 10, characterized in that the blood treatment machine has at least one pump that intermittently conveys a fluid volume at a specific frequency.

12. A method in accordance with claim 1, characterized in that the monitoring is continuous.

13. A method in accordance with claim 1, characterized in that a plurality of Fourier coefficients of higher harmonic Fourier series are calculated that are each compared with an associated reference value.

14. A blood treatment machine in accordance with claim 10, characterized in that the blood treatment machine has at least one peristaltic pump, that intermittently conveys a fluid volume at a specific frequency.

* * * * *